(12) United States Patent
Hoffmann et al.

(10) Patent No.: US 12,144,512 B2
(45) Date of Patent: Nov. 19, 2024

(54) FOOTSWITCH FOR CONTROLLING SURGICAL INSTRUMENTS AND RELATED ACCESSORIES

(71) Applicant: Stryker Corporation, Kalamazoo, MI (US)

(72) Inventors: Aaron Levi Hoffmann, Plainwell, MI (US); John Andrew Snodgrass, Plainwell, MI (US)

(73) Assignee: Stryker Corporation, Portage, MI (US)

( * ) Notice: Subject to any disclaimer, the term of this patent is extended or adjusted under 35 U.S.C. 154(b) by 540 days.

(21) Appl. No.: 17/534,497

(22) Filed: Nov. 24, 2021

(65) Prior Publication Data

US 2022/0160372 A1     May 26, 2022

Related U.S. Application Data

(60) Provisional application No. 63/118,174, filed on Nov. 25, 2020.

(51) Int. Cl.
*H01H 3/14*     (2006.01)
*A61B 17/15*     (2006.01)
*A61B 17/16*     (2006.01)
*A61B 17/00*     (2006.01)
*H01H 21/26*     (2006.01)

(52) U.S. Cl.
CPC .......... *A61B 17/1626* (2013.01); *A61B 17/15* (2013.01); *A61B 2017/00039* (2013.01); *A61B 2017/00137* (2013.01); *A61B 2017/00973* (2013.01); *H01H 21/26* (2013.01)

(58) Field of Classification Search
CPC ............. H01H 21/26; H01H 2300/014; H01H 25/006; H01H 3/14; H01H 9/06; H01H 13/16; A61B 17/1626; A61B 17/15; A61B 2017/00039; A61B 2017/00137; A61B 2017/00973; A61B 17/14; A61B 17/00; A61B 2090/033
See application file for complete search history.

(56) References Cited

U.S. PATENT DOCUMENTS

| | | | |
|---|---|---|---|
| 5,807,077 A | 9/1998 | Lamanna | |
| 8,465,473 B2 | 6/2013 | Horvath | |
| 9,271,806 B2 | 3/2016 | Tran et al. | |
| 9,795,507 B2 | 10/2017 | Hajishah et al. | |
| 10,115,542 B1 * | 10/2018 | Tsai | H01H 13/705 |

(Continued)

*Primary Examiner* — Ahmed M Saeed
(74) *Attorney, Agent, or Firm* — Howard & Howard Attorneys PLLC

(57) ABSTRACT

A surgical footswitch for controlling a surgical instrument. The surgical footswitch includes a base. A treadle is rotatably coupled to the base to operate the surgical instrument. A foot guard is also rotatably coupled to the base. A blocking portion of the foot guard is configured to prevent physical access to the treadle in a lateral direction in a first position and permit access to the treadle in a lateral direction in a second position. A floor engagement portion of the foot guard engages a floor surface when the blocking portion is in the first position. The floor engagement portion is spaced from the floor surface when the blocking portion is in the second position. The floor engagement portion permits physical access to the treadle in a longitudinal direction when the blocking portion is in both the first position and the second position.

20 Claims, 6 Drawing Sheets

(56) References Cited

U.S. PATENT DOCUMENTS

| | | | |
|---|---|---|---|
| 11,094,483 B2 * | 8/2021 | Poncella | H01H 13/85 |
| 11,551,891 B2 * | 1/2023 | Kurma Raju | H01H 37/323 |
| 2005/0253643 A1 * | 11/2005 | Inokawa | G06F 3/0421 |
| | | | 29/25.35 |
| 2006/0145540 A1 | 7/2006 | Mezhinsky | |
| 2019/0117322 A1 | 4/2019 | Laubenthal et al. | |
| 2020/0093507 A1 | 3/2020 | James et al. | |
| 2021/0307847 A1 | 10/2021 | Aubenthal et al. | |

\* cited by examiner

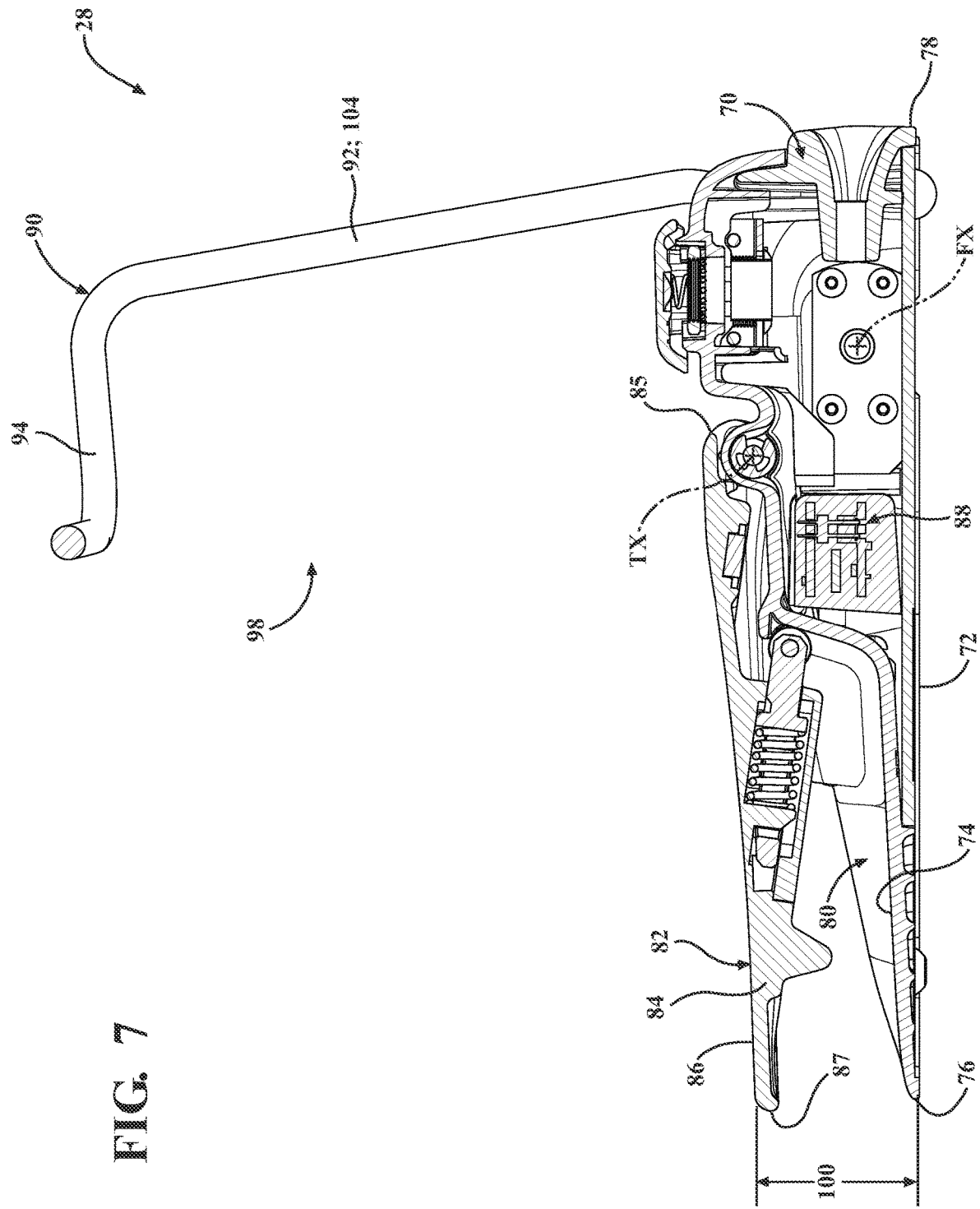

FOOTSWITCH FOR CONTROLLING SURGICAL INSTRUMENTS AND RELATED ACCESSORIES

This application claims priority to and the benefit of U.S. Provisional Patent Application No. 63/118,174, filed on Nov. 25, 2020, the entire contents of which are hereby incorporated by reference.

BACKGROUND

Conventional medical and surgical procedures routinely involve the use of surgical tools and instruments which allow surgeons to approach and manipulate surgical sites. By way of non-limiting example, the surgical instruments may include bone drills, saws, drivers, joint shavers, etc. Surgical instruments typically have functions controlled by hand-operated controls or foot pedals and/or switches placed on the floor of the operating room, which are operated by the surgeon. The foot controls may control functions such as on/off activation, speed or intensity, direction of movement of the tool, mode of operation, etc. The use of foot controls, rather than hand-operated controls, allows the surgeon to adjust various modes and settings of the tools (e.g., speed, intensity) themself, without having to put a tool down, change hands, touch potentially contaminated surfaces with their hands, or take their eyes off the patient.

While footswitches are routinely utilized to assist in the performance of a variety of different types of medical and/or surgical procedures, there is a need in the art to continuously improve such footswitches.

SUMMARY

With the scope of the invention defined by the claims included herein without limiting effect of the Summary, a first aspect of the present disclosure is directed to a surgical footswitch for controlling a surgical instrument. The surgical footswitch includes a base having a bottom surface for resting on a floor surface and a top surface opposite the bottom surface. A treadle is disposed above the top surface of the base. The treadle includes a treadle body having a first end rotatably coupled to the base and a second end opposite the first end. The treadle body is rotatable about a treadle axis. The surgical system also includes a foot guard. The foot guard includes a blocking portion coupled to the base. The blocking portion is movable to a first position in which physical access to the treadle body in a lateral direction is prevented. The blocking portion is also moveable to a second position in which physical access to the treadle body in the lateral direction is permitted. The foot guard also includes a floor engagement portion extending from the blocking portion. The floor engagement portion is configured to engage the floor surface when the blocking portion is in the first position. The floor engagement portion is configured to be spaced from the floor surface when the blocking portion is in the second position. The floor engagement portion is configured to permit physical access to the treadle body in a longitudinal direction when the blocking portion is in both the first position and the second position.

A second aspect of the present disclosure is directed to a surgical footswitch for controlling a surgical instrument. The surgical footswitch includes a base having a bottom surface for resting on a floor surface and a top surface opposite the bottom surface. The base has a proximal end and a distal end opposite the proximal end. The surgical footswitch includes a treadle disposed above the top surface of the base. The treadle includes a treadle body having a first end rotatably coupled to the base and a second end opposite the first end. The treadle body is rotatable about a treadle axis. The treadle axis is adjacent the distal end of the base. The surgical footswitch further includes a foot guard. The foot guard includes a first portion coupled to the base. The first portion is movable to a first position in which physical access to the treadle body in a lateral direction is prevented. The first portion is also moveable to a second position in which physical access to the treadle body in the lateral direction is permitted. The foot guard also includes a second portion extending from the first portion. The second portion is configured to permit physical access to the treadle body in a longitudinal direction adjacent the proximal end of the base when the first portion is in either of the first position and the second position.

BRIEF DESCRIPTION OF THE DRAWINGS

Advantages of the present invention will be readily appreciated as the same becomes better understood by reference to the following detailed description when considered in connection with the accompanying drawings wherein:

FIG. 7 is a sectional view of the footswitch with the foot guard in the second position taken along lines 7-7 of FIG. 6.

DETAILED DESCRIPTION

Figure 1:
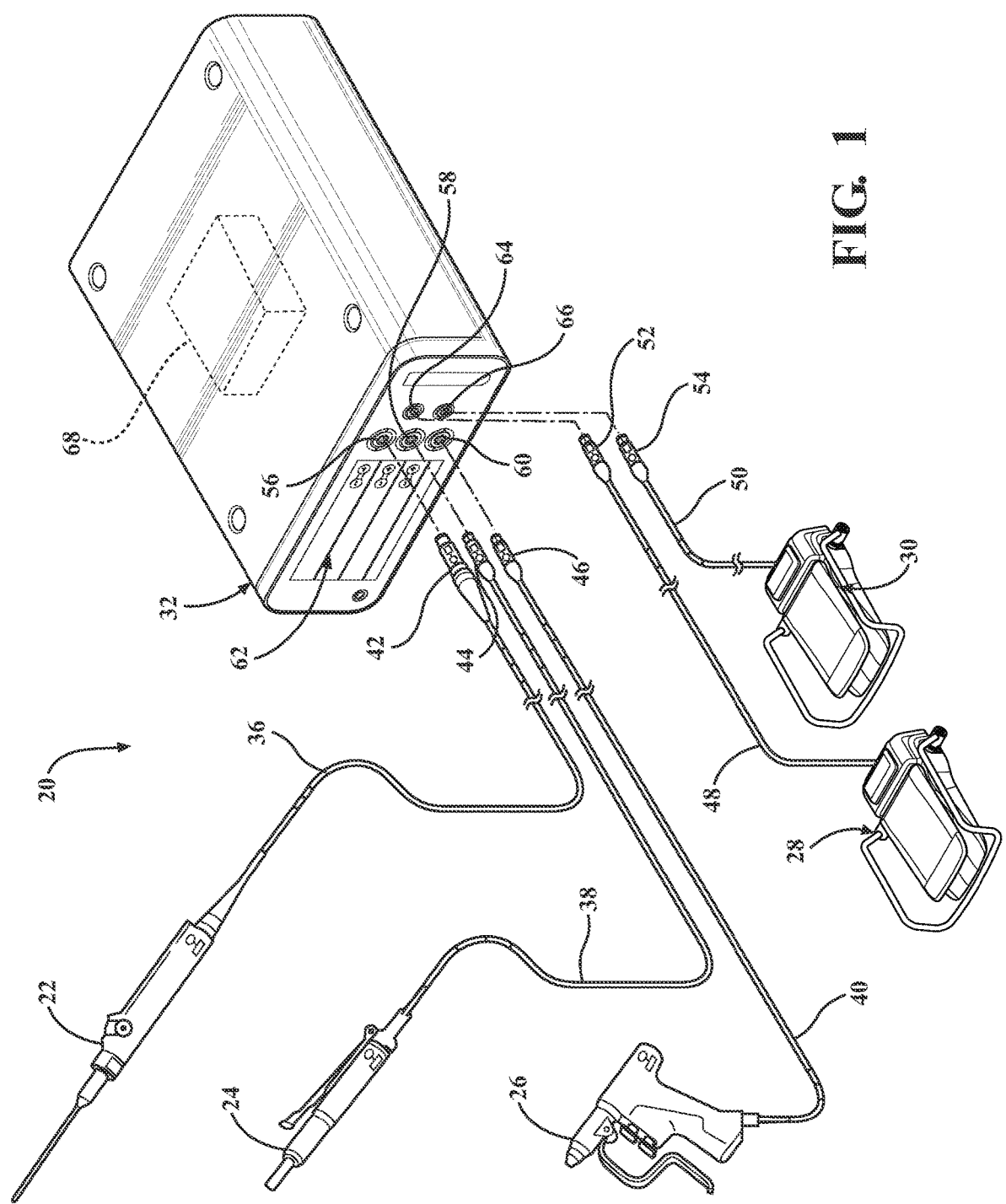
FIG. 1 is a perspective view of a surgical system including footswitches, a console, and surgical instruments.
Figure 2:
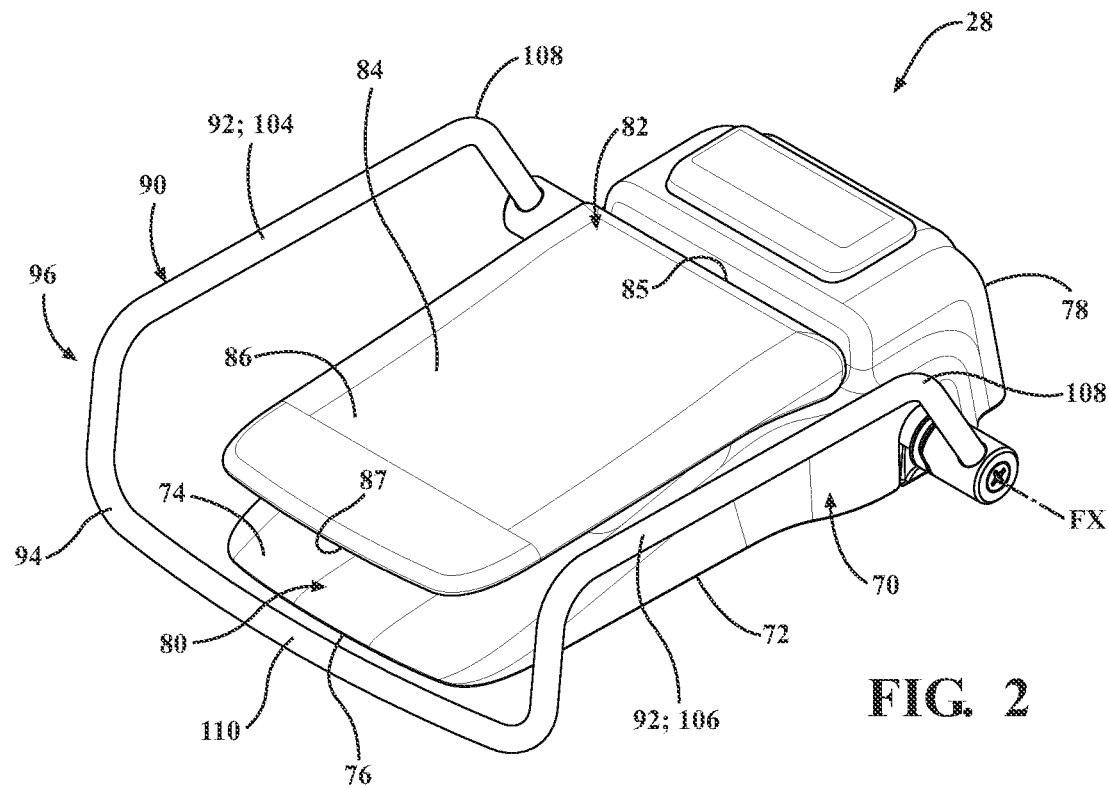
FIG. 2 is a perspective view of a footswitch of the surgical system with a foot guard in a first position.

Referring to FIG. 1, a surgical system 20 is shown. The surgical system 20 may comprise one or more handheld surgical instruments 22, 24, 26, one or more footswitches 28, 30, and a console 32 for associating one or more of the instruments 22, 24, 26 with one or more of the footswitches 28, 30 to control the associated instruments during a surgical procedure. The system 20 is shown in FIG. 1 as, for exemplary purposes, controlling three handheld surgical instruments 22, 24, 26, but in other configurations, the system can control one, two, four, five, or any suitable number and type of instruments. Furthermore, system 20 is shown as, for exemplary purposes, comprising two footswitches 28, 30, but in other configurations, the system may comprise one, three, four, five, or any number of footswitches or other types of input devices. An illustrative configuration of an exemplary footswitch 28, which may be used as either of footswitches 28 and/or 30, is described below and shown in FIGS. 2-7.

Each one of the first, second, and third handheld surgical instruments 22, 24, 26 is configured to perform one or more predetermined functions in the treatment or care of a patient. Each instrument 22, 24, 26 can utilize one or more components that require electricity. As one example, one or more of the instruments may comprise a specialty drill such as one sold under the brand name CORE UNIVERSAL SERIES by Stryker Instruments of Kalamazoo, Mich., United States. Other examples of the instruments may comprise: a highpowered tapered drill, such as one sold under the brand name CORE SUMEX DRILL by Stryker Instruments; a modular handpiece such as one sold under the brand name CORE UNIVERSAL DRIVER by Stryker Instruments; a high-speed pencil-grip drill such as one sold under the brand name CORE MICRO DRILL by Stryker; a pneumatic drill such as one sold under the brand name MAESTRO DRILL by Stryker; a drill for intraoperative procedures such as one sold under the brand name ARIA MRI DRILL SYSTEM by Stryker; a drill for oral surgery such as one sold under the brand name CORE IMPACTION DRILL by Stryker; a drill for ENT surgery sold under the brand name SABER DRILL by Stryker; a sagittal saw, an oscillating saw, or a reciprocating saw, such as those sold under the brand name MICRO SAW by Stryker; various burs for small bone procedures such as those sold under the brand names ELITE BUR, ZYPHR BUR, MIS BUR, and TPS BUR; a microdebrider such as one sold under the brand name ESSX MICRODEBRIDER; an ultrasonic aspirator such as one sold under the brand name SONOPET ULTRASONIC ASPIRATOR by Stryker; a pair of bipolar forceps such as one sold under the brand name SILVERGLIDE BIPOLAR FORCEPS by Stryker.

Other handheld surgical instruments sold by Stryker or any manufacturer are also contemplated. For instance, electrosurgical devices, ultrasound devices, and other surgical devices may also be employed. Electrosurgical instruments and others like them can be of any suitable type known in the art, including those that use diathermy with either unipolar or bipolar current (commonly referred to simply as unipolar devices and bipolar devices), and advanced devices such as harmonic scissors and argon beam and laser devices. The illustrated shapes and other structural features of instruments 22, 24, 26 as depicted in FIG. 1 are not intended to describe the instruments specifically but rather are intended only to convey the general concept that various instruments can be used. Indeed, it is important to note that the present disclosure facilitates the integration of instruments that may have different functions and other characteristics in terms of how they respond to their associated device user controls (not shown) and in terms of the signals produced by their device user controls that characterize their operation. For example, the instruments 22, 24, 26 can have functions that differ from those of each other as a result of the first handheld surgical instrument 22 being, for example, a unipolar device, while second handheld surgical instrument 24 is, for example, a bipolar device, and the third handheld surgical instrument 26 is a harmonic device. In addition, it may be that, for example, the first and second handheld surgical instruments 22 and 24 have different operating characteristics from each other because they require signals of different voltages from each other. The various devices may be produced by different manufacturers or be different versions or models of a device. Regardless of any such differences, the system 20 ensures that the instruments to which it is connected can be controlled by the first and second footswitches 28, 30 or the console 32.

Additionally, while handheld surgical instruments are emphasized in this disclosure, other types of medical devices may also be used in place thereof in certain configurations. For example, suitable medical devices that could be used in conjunction with the console, include, but are not limited to, patient therapy devices, patient monitoring devices, or surgical instruments that are not handheld, such as surgical robots, hospital beds, lighting systems, cameras, etc. As such, the term "handheld surgical instrument" may be interchanged with these medical devices throughout this disclosure.

The first, second, and third handheld surgical instruments 22, 24, 26 may comprise a corresponding one of connector lines 36, 38, 40. Each connector line 36, 38, 40 may terminate at one end that is coupled to a corresponding one of the instruments 22, 24, 26 and terminate at an opposing end with a corresponding one of plugs 42, 44, 46 configured to engage the console 32. In other configurations, the connector lines may terminate with a socket or any type of connector.

In the illustrated configuration, footswitch 28 and/or footswitch 30 can comprise certain features of a footswitch sold under the brand name UNI-DIRECTIONAL FOOTSWITCH by Stryker, a footswitch sold under the brand name TPS FOOT SWITCH by Stryker, or any other type of input device sold by Stryker or another manufacturer. It is also contemplated that the footswitch 28 may also comprise certain features, including operation and control of the features, disclosed in U.S. Patent Publication No. 2019/0117322, filed Dec. 14, 2018, the contents of which are incorporated herein by reference in their entirety. Each footswitch 28 may include one or more sensors, such as Hall-effect sensors, magnetic sensors, or other suitable sensors, that generate signals in response to depression of the footswitch.

The footswitches 28, 30 may comprise a corresponding one of connector lines 48, 50. Each connector line 48, 50 may terminate at one end that is coupled to a corresponding one of the footswitches 28, 30 and terminate at an opposing end with a corresponding one of plugs 52, 54 configured to engage the console 32. In other configurations, the connector lines 48, 50 may terminate with a socket or any type of connector. In other configurations, one or both footswitches 28, 30 may operate the surgical instruments 22, 24, 26 remotely, i.e., without connector lines 48, 50. In still other configurations, one or both footswitches 28, 30 may operate the surgical instruments directly, i.e., without the console 32. In such a configuration, certain input devices of a footswitch 28 may control operations of a single surgical instrument 22.

The console 32 may comprise first, second, and third instrument ports 56, 58, 60. The plugs 42, 44, 46 of the connector lines 36, 38, 40 may be associated with the handheld surgical instruments 22, 24, 26 are capable of being connected to a corresponding one of the first, second, and third instrument ports 56, 58, 60. It is contemplated that the system 20 can instead comprise one, two, four, or any number of instrument ports positioned on any suitable portion of the console 32. Furthermore, the console 32 comprises first and second footswitch ports 64, 66. The plugs 52, 54 of the connector lines 48, 50 associated with the footswitches 28, 30 are capable of being connected to the first and second footswitch ports 64, 66. The first and second footswitch ports 64, 66 are spaced apart from the display 62, such that the first, second, and third instrument ports 56, 58, 60 are positioned between the footswitch ports 64, 66 and the display 62. However, other configurations of the instrument ports 56, 58, 60, the footswitch ports 64, 66, and the display 62 are contemplated.

A controller 68 configured to associate one of the first, second, and third instrument ports 56, 58, 60 with the first footswitch port 64, such that the first footswitch 28 is operable to actuate a function of the handheld surgical instruments connected to the associated instrument port. Similarly, the controller 68 is configured to associate another one of the first, second, and third instrument ports 56, 58, 60, with the second footswitch port 66 such that the second footswitch 30 is operable to actuate a function of the handheld surgical instrument connected with the associated instrument port. It is contemplated that the controller 68 may associate the same instrument port with both of the first and second footswitch ports 64, 66, such that the footswitches 28, 30 are operable to actuate a function of the same handheld surgical instrument connected to the associated instrument port. While the controller 68 illustrated in FIG. 1 is shown being coupled to the console 32, it is contemplated that the controller 68 may instead be coupled to the surgical instrument or be coupled to the footswitch. The console 32 is capable of being coupled to a power source (not shown) to receive power therefrom and deliver the same to any one or more of the instruments 22, 24, 26, and the footswitches 28, 30.

Referring to FIGS. 2-7, one configuration of the footswitch 28 is illustrated. The footswitch 28 comprises a base 70 having a bottom surface 72 for resting on a floor surface. The base 70 may comprise one or more projections (e.g., feet, legs, stand-offs, etc.) extending away from the bottom surface 72 of the base 70 for resting on a floor surface to space the bottom surface 72 of the base 70 from the floor surface. The base 70 also comprises a top surface 74 opposite the bottom surface 72. The base 70 has a proximal end 76 and a distal end 78 opposite the proximal end 76. The base 70 may define a recess 80 extending from the proximal end 76 toward the distal end 78 to provide clearance for the treadle 82 as described below.

The footswitch 28 comprises a treadle 82 disposed above the top surface 74 of the base 70. In some configurations the treadle 82 may also be referred to as a foot pedal. The treadle 82 comprises a treadle body 84 having a first end 85 rotatably coupled to the base 70 and a second end 87 opposite the first end 85. The treadle body 84 has a top surface 86 where a user may place their foot to move the treadle body 84 relative to the base 70. The treadle body 84 is configured to rotate about a treadle axis TX. The first end 85 of the treadle body 84 is adjacent the treadle axis TX. In the configurations illustrated in FIGS. 2-7, the treadle axis TX is adjacent the distal end 78 of the base 70. In other configurations the treadle axis TX is adjacent the proximal end of the base 70.

The treadle 82 acts as an input device for controlling one or more functions of one or more of the surgical instruments 22, 24, 26 described above. In some configurations, the treadle body 84 is configured to be received by the recess 80 of the base 70. The treadle body 84 being received by the recess 80 of the base 70 may provide low-profile arrangement of the treadle 82 for the user by allowing the treadle body 84 to be disposed closer to a floor surface. When the treadle body 84 is closer to the floor surface, the user may more easily be able to keep their heel on the ground as they manipulate or depress the treadle body 84 with the sole or end portion of their foot. Keeping the user's heel on the ground may reduce fatigue and stress on the user during a surgical procedure. In other configurations where the base 70 does not define a recess 80 for receiving the treadle body 84, the arrangement of the treadle body 84 relative to the base 70 may still permit the user to keep their heel on the floor surface during operation of the treadle 82.

The footswitch 28 may comprise a sensor 88 configured to generate signals that may be received by the controller 68 for controlling one or more of the surgical instruments 22, 24, 26 responsive to movement of the treadle body 84 about the treadle axis TX relative to the base 70. In the configurations illustrated in FIGS. 2-7, the sensor 88 comprises a Hall-effect sensor. It is contemplated that in other configurations, the footswitch 28 may comprise other sensors for generating signals to control one or more surgical instruments 22, 24, 26 responsive to movement of the treadle body 84 relative to the base 70.

As shown in FIGS. 2-7, the footswitch 28 comprises a foot guard 90. The foot guard 90 comprises a blocking portion 92, sometimes referred to as a first portion, for selectively preventing access to the treadle body 84 by the user in lateral directions in certain positions. The foot guard 90 also comprises a floor engagement portion 94, sometimes referred to as a second portion, extending from the blocking portion 92. The floor engagement portion 94 may provide rigidity and/or stability to the foot guard 90 to retain a position of the blocking portion 92 relative to the treadle 82 and the base 70. For instance, the floor engagement portion 94 may mitigate deflection of the blocking portion 92 of the foot guard 90 when a user unintentionally applies force to the blocking portion 92 while operating the treadle 82.

The blocking portion 92 of the foot guard 90 is coupled to the base 70 and movable to a first position 96 (FIGS. 2-4) in which physical access to the treadle body 84 in a lateral direction is prevented and a second position 98 (FIGS. 5-7) in which physical access to the treadle body 84 in the lateral direction is permitted. The lateral direction may further be defined as being a direction parallel to the treadle axis TX. The blocking portion 92 of the foot guard 90 is configured to rotate about a foot guard axis FX. The foot guard axis FX may be distal the treadle axis TX and disposed between the treadle axis TX and the distal end 78 of the base 70.

The foot guard 90 may also be used as a carrying handle to reposition the footswitch 28 or to transport the footswitch 28 from one location to another. This function of the foot guard 90 is particularly useful when the blocking portion 92 of the foot guard 90 is in the second position 98.

The base 70 may permit physical access to the treadle body 84 in the lateral direction when the blocking portion 92 of the foot guard 90 is in the second position 98. In other words, when the foot guard 90 is not preventing access to the treadle body 84 in the lateral direction, the base 70 may be free of features that would prevent access to the treadle body 84 in the lateral direction.

Users may have different preferences during a surgical procedure regarding whether they may be permitted to access the treadle 82 in a lateral direction to operate (e.g., manipulate or depress) the footswitch 28. In some instances, users prefer freedom to access the treadle 82 using many different approaches i.e., access angles/directions, including in a lateral direction. In other instances, users prefer only being able to access the treadle 82 when they approach from the front or proximal end 76 of the base 70. By permitting the foot guard 90 to move relative to the base 70 and the treadle 82 as described, the foot guard 90 accommodates both preferences.

Figure 4:
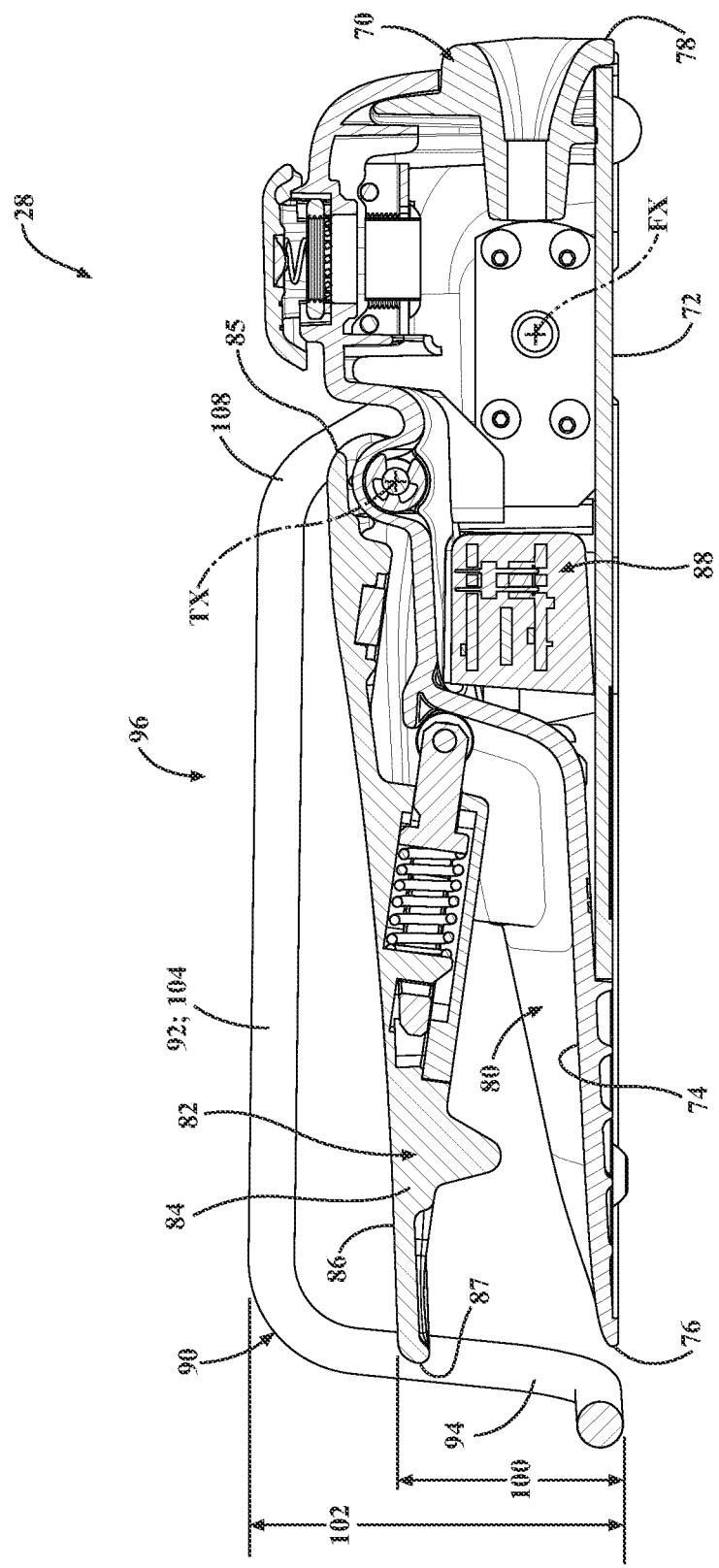
FIG. 4 is a sectional view of the footswitch with the foot guard in the first position taken along lines 4-4 of FIG. 3.
Figure 5:
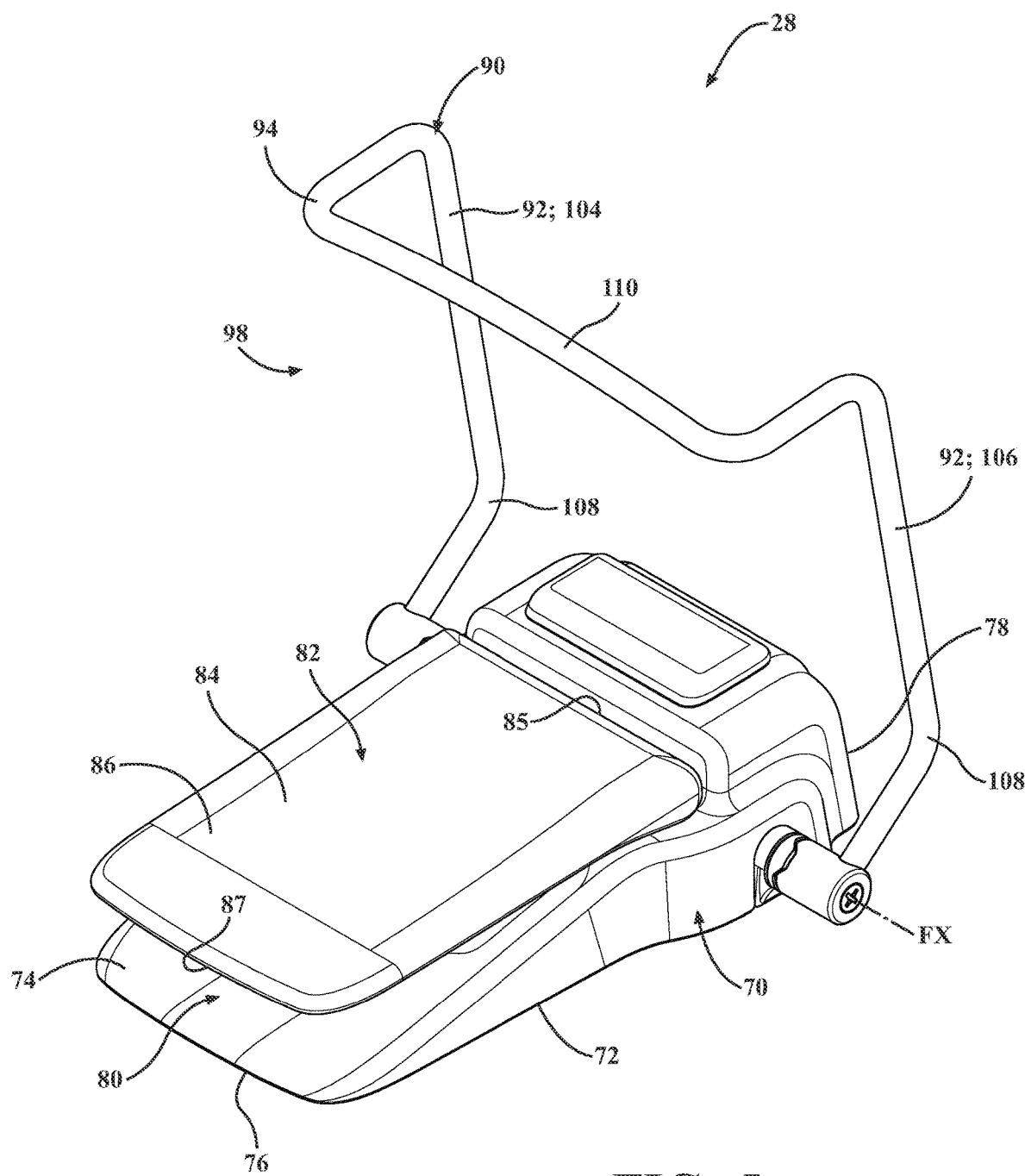
FIG. 5 is a perspective view of the footswitch of the surgical system with the foot guard in a second position.
Figure 6:
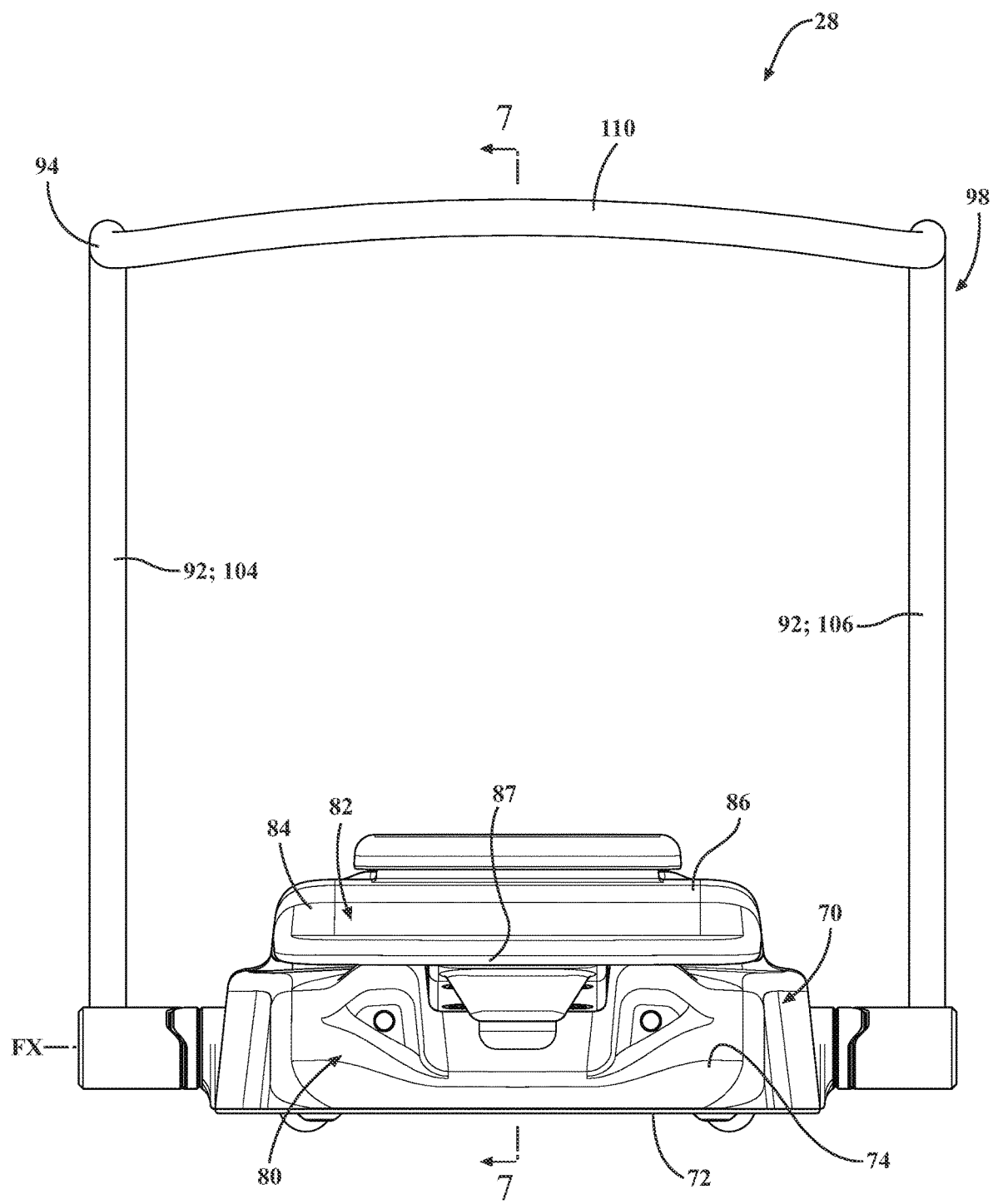
FIG. 6 is an elevation view of the footswitch with the foot guard in the second position.

As shown in FIG. 4, the blocking portion 92 of the foot guard 90 may be configured to prevent physical access to the treadle body 84 in the lateral direction at heights above the floor surface. More specifically, a first height 100 defined between the bottom surface 72 of the base 70 and the second end 87 of the treadle body 84 may be less than a second height 102 defined between the bottom surface 72 of the base 70 and the blocking portion 92 when the blocking portion 92 of the foot guard 90 is in the first position 96. In some configurations, the blocking portion 92 of the foot guard 90 is disposed above the treadle body 84 between at least the first and second ends 85, 87 of the treadle body 84 when the blocking portion 92 of the foot guard 90 is in the first position 96. In other configurations, at least part of the blocking portion 92 of the foot guard 90 is disposed above the treadle body 84 in the first position 96, the second position 98, and each position (not shown) therebetween. While access to the treadle body 84 in a lateral direction is restricted by the blocking portion 92 of the foot guard 90 when the blocking portion 92 of the foot guard 90 is in the first position 96, operation of the treadle body 84 may be possible in a longitudinal direction when the blocking portion 92 of the foot guard 90 is in both the first and second positions 96, 98.

The blocking portion 92 of the foot guard 90 may comprise a first arm 104 and a second arm 106 spaced from and moveable with the first arm 104. Each of the first and second arms 104, 106 may comprise first ends rotatably coupled to the base 70 and second ends opposite the first ends. The first and second arms 104, 106 may be configured to at least partially surround the treadle body 84 such that the treadle body 84 is disposed between the first and second arms 104, 106. The first and second arms 104, 106 may be configured to move to the first and second positions 96, 98. While the first and second arms 104, 106 of the blocking portion 92 may not prevent all access to the treadle body 84 in a lateral direction, as there is limited space above and below the first and second arms 104, 106, the arrangement of the first and second arms 104, 106 in the configuration illustrated in FIGS. 2-7 is particularly advantageous in surgical procedures where the user has their heel on the ground and is pivoting their foot to manipulate the treadle body 84.

Figure 3:
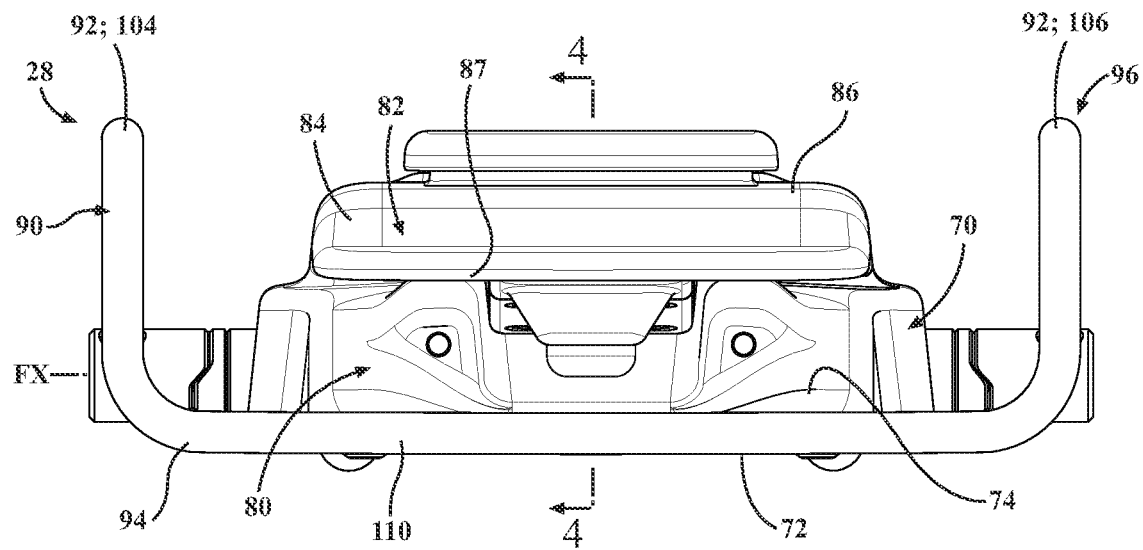
FIG. 3 is an elevation view of the footswitch with the foot guard in the first position.

As shown in FIGS. 3 and 4, the foot guard axis FX may be disposed beneath the treadle axis TX, i.e., between the bottom surface 72 of the base 70 and the treadle axis TX. In such a configuration, one or both of the first and second arms 104, 106 of the blocking portion 92 of the foot guard 90 may comprise one or more bends 108 proximal the first end of the first and second arms 104, 106 so that at least part of the blocking portion 92 of the foot guard 90 extends above the treadle body 84.

The floor engagement portion 94 of the foot guard 90 extends from the blocking portion 92. The floor engagement portion 94 is configured to engage the floor surface when the blocking portion 92 is in the first position 96. The floor engagement portion 94 is further configured to be spaced from the floor surface when the blocking portion 92 is in the second position 98. The floor engagement portion 94 is configured to permit physical access to the treadle body 84 in a longitudinal direction when the blocking portion 92 is in both the first position 96 and the second position 98. In some configurations, the floor engagement portion 94 establishes the first position 96 of the blocking portion 92 of the foot guard 90. Said differently, the blocking portion 92 of the foot guard 90 may be in the first position 96 when the floor engagement portion 94 engages the floor surface. The longitudinal direction may be further defined as being perpendicular to the treadle axis TX. The longitudinal direction may be even further defined as also being generally parallel to the bottom surface 72 of the base 70.

The floor engagement portion 94 of the foot guard 90 is configured to permit physical access to the treadle body 84 in the longitudinal direction at the first height 100 above the floor surface defined between the bottom surface 72 of the base 70 and the second end 87 of the treadle body 84 when the blocking portion 92 of the foot guard 90 is in both the first position 96 and the second position 98. In some configurations, the floor engagement portion 94 comprises a connector 110 coupled to the second ends of the first and second arms 104, 106 of the blocking portion 92 of the foot guard 90. In such a configuration at least a portion of the connector 110 would be configured to engage the floor surface. The connector 110 and the first and second arms 104, 106 of the blocking portion 92 may be monolithically formed. In other configurations, the floor engagement portion 94 may extend downwardly toward the floor surface from one or both the second ends of the first and second arms 104, 106 of the blocking portion 92 of the foot guard 90 to engage the floor surface and prevent continued movement of the blocking portion 92 past the first position 96.

While the floor engagement portion 94 of the foot guard 90 is configured to engage the floor surface when the blocking portion 92 of the foot guard 90 is in the first position 96, it is contemplated that the floor engagement portion 94 may be configured otherwise. For instance, the floor engagement portion 94 may instead engage the top surface 74 of the base 70 or another surface to prevent continued movement of the blocking portion 92 past the first position 96. In such a configuration, the floor engagement portion 94 would still function to mitigate deflection of the blocking portion 92 of the foot guard 90.

The foregoing description is merely illustrative in nature and is in no way intended to limit the disclosure, its application, or uses. The broad teachings of the disclosure can be implemented in a variety of forms. Therefore, while this disclosure includes particular configurations, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the configurations is described above as having certain features, any one or more of those features described with respect to any example of the disclosure can be implemented in and/or combined with features of any of the other configurations, even if that combination is not explicitly described. In other words, the described examples are not mutually exclusive, and permutations of one or more examples with one another remain within the scope of this disclosure.

Spatial and functional relationships between elements (for example, between controllers, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements.

As used herein, the phrase at least one of A, B, and C should be construed to mean a logical (A OR B OR C), using a non-exclusive logical OR, and should not be construed to mean "at least one of A, at least one of B, and at least one of C." The term subset does not necessarily require a proper subset. In other words, a first subset of a first set may be coextensive with (equal to) the first set.

In this application, including the definitions below, the term "controller 68" may be replaced with the term "circuit." The term "controller 68" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The controller 68 may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The controller 68 may communicate with other controllers using the interface circuit(s). Although the controller 68 may be depicted in the present disclosure as logically communicating directly with other controllers, in various implementations the controller 68 may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the controller 68 may be distributed among multiple controllers that are connected via the communications system. For example, multiple controllers may implement the same functionality distributed by a load balancing system. In a further example, the functionality of the controller 68 may be split between a server (also known as remote, or cloud) controller and a client (or, user) controller.

Some or all hardware features of the controller 68 may be defined using a language for hardware description, such as IEEE Standard 1364-2005 (commonly called "Verilog") and IEEE Standard 10182-2008 (commonly called "VHDL"). The hardware description language may be used to manufacture and/or program a hardware circuit. In some implementations, some or all features of a controller may be defined by a language, such as IEEE 1666-2005 (commonly called "SystemC"), that encompasses both code, as described below, and hardware description.

The term code, as used above, may include software, firmware, and/or microcode, and may refer to programs, routines, functions, classes, data structures, and/or objects. The term shared processor circuit encompasses a single processor circuit that executes some or all code from multiple controllers. The term group processor circuit encompasses a processor circuit that, in combination with additional processor circuits, executes some or all code from one or more controllers. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple controllers. The term group memory circuit encompasses a memory circuit that, in combination with additional memories, stores some or all code from one or more controllers.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general-purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SSENSORLINK, and Python®.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A surgical footswitch for controlling a surgical instrument, the surgical footswitch comprising:
   a base having a bottom surface for resting on a floor surface and a top surface opposite the bottom surface;
   a treadle disposed above the top surface of the base, the treadle comprising a treadle body having a first end rotatably coupled to the base and a second end opposite the first end, and the treadle body rotatable about a treadle axis; and
   a foot guard comprising,
      a blocking portion coupled to the base and movable to a first position in which physical access to the treadle body in a lateral direction is prevented and a second position in which physical access to the treadle body in the lateral direction is permitted, and
      a floor engagement portion extending from the blocking portion, the floor engagement portion configured to engage the floor surface when the blocking portion is in the first position, and the floor engagement portion configured to be spaced from the floor surface when the blocking portion is in the second position, and the floor engagement portion configured to permit physical access to the treadle body in a longitudinal direction when the blocking portion is in both the first position and the second position.

2. The surgical footswitch of claim 1, wherein the longitudinal direction is further defined as being perpendicular to the treadle axis, and wherein the lateral direction is further defined as being a direction parallel to the treadle axis.

3. The surgical footswitch of claim 1, wherein the floor engagement portion of the foot guard is configured to permit physical access to the treadle body in the longitudinal direction at heights above the floor surface defined between the bottom surface of the base and the second end of the treadle body when the blocking portion of the foot guard is in both the first position and the second position.

4. The surgical footswitch of claim 1, wherein the blocking portion of the foot guard is configured to prevent physical access to the treadle body in the lateral direction at heights above the floor surface defined between the bottom surface of the base and the second end of the treadle body when the blocking portion of the foot guard is in the first position.

5. The surgical footswitch of claim 1, wherein the base permits physical access to the treadle body in the lateral direction when the blocking portion of the foot guard is in the second position.

6. The surgical footswitch of claim 1, wherein the blocking portion of the foot guard comprises a first arm and a second arm spaced from and moveable with the first arm, with the treadle body disposed between the first and second arms, the first and second arms each having a first end rotatably coupled to the base and a second end opposite the first end, and the first and second arms configured to move to the first and second positions.

7. The surgical footswitch of claim 6, wherein the floor engagement portion of the foot guard comprises a connector coupled to the second ends of the first and second arms of the blocking portion of the foot guard.

8. The surgical footswitch of claim 7, wherein the first arm, the second arm, and the connector are monolithically formed.

9. The surgical footswitch of claim 1, wherein at least part of the blocking portion of the foot guard is disposed above the treadle body in the first position, the second position, and each position therebetween.

10. The surgical footswitch of claim 1, further comprising a sensor configured to generate signals for controlling the surgical instrument responsive to movement of the treadle body about the treadle axis when the blocking portion of the foot guard is in both the first and second positions.

11. A surgical footswitch for controlling a surgical instrument, the surgical footswitch comprising: a base having a bottom surface for resting on a floor surface and a top surface opposite the bottom surface, the base having a proximal end and a distal end opposite the proximal end; a treadle disposed above the top surface of the base, the treadle comprising a treadle body having a first end rotatably coupled to the base and a second end opposite the first end, and the treadle body rotatable about a treadle axis, with the treadle axis being adjacent the distal end of the base; and a foot guard comprising, a first portion coupled to the base and movable to a first position in which physical access to the treadle body in a lateral direction is prevented and a second position in which physical access to the treadle body in the lateral direction is permitted, and a second portion extending from the first portion, the second configured to permit physical access to the treadle body in a longitudinal direction adjacent the proximal end of the base when the first portion is in both the first position and the second position, wherein the first portion of the foot guard is configured to prevent physical access to the treadle body in the lateral direction at heights above the floor surface defined between the bottom surface of the base and the second end of the treadle body when the first portion of the foot guard is in the first position.

12. The surgical footswitch of claim 11, wherein the first portion of the foot guard is rotatable about a foot guard axis, and wherein the foot guard axis is distal the treadle axis between the treadle axis and the distal end of the base.

13. The surgical footswitch of claim 11, wherein the longitudinal direction is further defined as being perpendicular to the treadle axis, and wherein the lateral direction is further defined as being a direction parallel to the treadle axis.

14. The surgical footswitch of claim 11, wherein the second portion of the foot guard is configured to permit physical access to the treadle body in the longitudinal direction at heights above the floor surface defined between the bottom surface of the base and the second end of the treadle body when the first portion of the foot guard is in both the first position and the second position.

15. The surgical footswitch of claim 11, wherein the base permits physical access to the treadle body in the lateral direction when the first portion of the foot guard is in the second position.

16. The surgical footswitch of claim 11, wherein the first portion of the foot guard comprises a first arm and a second arm spaced from and moveable with the first arm, with the treadle body disposed between the first and second arms, the first and second arms each having a first end rotatably coupled to the base and a second end opposite the first end, and the first and second arms configured to move to the first and second positions.

17. The surgical footswitch of claim 16, wherein the second portion of the foot guard comprises a connector coupled to the second ends of the first and second arms of the first portion of the foot guard.

18. The surgical footswitch of claim 17, wherein the first arm, the second arm, and the connector are monolithically formed.

19. The surgical footswitch of claim 11, wherein at least part of the first portion of the foot guard is disposed above the treadle body in the first position, the second position, and each position therebetween.

20. The surgical footswitch of claim 11, further comprising a sensor configured to generate signals for controlling the surgical instrument responsive to movement of the treadle body about the treadle axis when the first portion of the foot guard is in both the first and second positions.

\* \* \* \* \*